United States Patent
Matsunaga et al.

(10) Patent No.: US 7,396,543 B2
(45) Date of Patent: Jul. 8, 2008

(54) PROCESS FOR PHYSICOCHEMICALLY PRODUCING GLYCOGEN AND GLYCOGEN OBTAINED THEREBY

(75) Inventors: Kazuyoshi Matsunaga, Okayama (JP); Takafumi Ishihara, Okayama (JP)

(73) Assignee: Bizen Chemical Co., Ltd., Okayama (JP)

(*) Notice: Subject to any disclaimer, the term of this patent is extended or adjusted under 35 U.S.C. 154(b) by 255 days.

(21) Appl. No.: 10/497,694

(22) PCT Filed: Dec. 6, 2002

(86) PCT No.: PCT/JP02/12832

§ 371 (c)(1), (2), (4) Date: Oct. 13, 2004

(87) PCT Pub. No.: WO03/048212

PCT Pub. Date: Jun. 12, 2003

(65) Prior Publication Data

US 2005/0048142 A1 Mar. 3, 2005

(30) Foreign Application Priority Data

| Dec. 7, 2001 | (JP) | ............................. 2001-375037 |
| Sep. 30, 2002 | (JP) | ............................. 2002-287924 |
| Oct. 21, 2002 | (JP) | ............................. 2002-306295 |

(51) Int. Cl.
*A61K 36/00* (2006.01)
*A61K 36/258* (2006.01)

(52) U.S. Cl. ....................... 424/725; 424/728

(58) Field of Classification Search ................. 424/725, 424/728
See application file for complete search history.

(56) References Cited

U.S. PATENT DOCUMENTS

| 1,190,953 | A | | 7/1916 | Renshaw |
| 3,238,193 | A | | 3/1966 | Ruschloff et al. |
| 3,875,317 | A | | 4/1975 | Ferguson |
| 3,876,501 | A | * | 4/1975 | Hanushewsky ............. 435/178 |
| 3,954,497 | A | | 5/1976 | Friese |
| 4,103,003 | A | | 7/1978 | Ashmead |
| 4,508,745 | A | | 4/1985 | Fulger et al. |
| 5,773,227 | A | * | 6/1998 | Kuhn et al. ................. 435/7.21 |

FOREIGN PATENT DOCUMENTS

| GB | 1284218 A | 8/1972 |
| JP | 10-234315 | 9/1998 |
| JP | 2003-088323 A | 3/2003 |
| KR | 1020000012173 | 3/2003 |

OTHER PUBLICATIONS

Trends Glycosci. Glycotechnol. 8:163-194, (http://www.gak.co.jp/TIGG/41MR3e.html).*
"Biochemistry of Glycogen" (http://www.uic.edu/classes/phar/phar332/Clinical_Cases/carbo%20metab%20cases/glycogen%20metab/Glycogen%20biochemistry.htm).*
"Structure of a Low Molecular Weight Form of Glycogen Isolated from the Liver in a Case of Glycogen Storage Disease", Edstrom, Ronald D., Journal of Biological Chemistry (1972), vol. 247, No. 5, Issue of Mar. 10, pp. 1360-1367.
"Low-Molecular Weight Glycogen Found in a Human with a Generalized Storage Disease", Edstrom, Ronald D., ARchives of Biochemistry and Biophysics (1970), pp. 293-295.
"Antitumer glycogen from scallops and the interrelationship of structure and antitumor activity", Yosiaki Takata, et al., J. Mar. Biotech., 6, pp. 208-213 (1998).
"Structure of a Low Molecular Weight Form of Glycogen Isolated from the Liver in a Case of Glycogen Storage Disease", by R.D. Edstrom, The Journal of Biological Chemistry, 247(5) 1360-1367, 1972.

* cited by examiner

*Primary Examiner*—Ruth A Davis
(74) *Attorney, Agent, or Firm*—Snell & Wilmer L.L.P.

(57) ABSTRACT

A method of producing glycogen is provided. The method comprises the step of heat- and pressure-treating a sugar-containing material under acidic conditions. The sugar-containing material is a polysaccharide or an oligosaccharide. Alternatively, the sugar-containing material is a plant material selected from the group consisting of Panax notoginseng, Yun Nan San-chi powder (trademark), Panax ginseng, wheat flour, soybean, soy flour, shiitake, and coffee extract residue. Representatively, the glycogen includes a molecule having a molecular weight of 10,000 or less. The glycogen has a specific rotation of $[\alpha]_D +197°$ and anomeric proton peaks at 5.37 ppm and 4.95 to 5.33 ppm in $^1$H NMR spectra.

3 Claims, 4 Drawing Sheets

(a)

(b)

(c)

(a)

(b)

US 7,396,543 B2

PROCESS FOR PHYSICOCHEMICALLY PRODUCING GLYCOGEN AND GLYCOGEN OBTAINED THEREBY

FIELD OF INVENTION

The present invention relates to a method of physicochemically producing glycogen from polysaccharides, such as starch, cellulose, dextran, pullulan, and the like, oligosaccharides, such as maltose and the like, and sugar-containing materials, such as wheat flour, Panax notoginseng, and the like which contain these saccharides. The present invention also relates to glycogen produced by this method and use thereof.

BACKGROUND OF THE INVENTION

Glycogen is a homopolysaccharide consisting of glucoses like starch, which is a storage polysaccharide in plants. Glycogen has a polymer structure in which D-glucoses are linked together with α1-4 glycoside linkages and a highly branched structure which has a branch per 8 to 10 glucose residues due to α1-6 glycoside linkage.

Glycogen is known as an animal storage polysaccharide. In animals, glycogen is contained in a granule form (glycogen granule) in almost all cells, particularly in liver and muscle in a large amount. Muscle glycogen is an energy source for muscle contraction. Liver glycogen is used to maintain blood sugar during fasting. The difference in the characters of glycogens corresponds to the difference in the functions thereof. The muscle glycogen has a molecular weight of 1-2 million. The liver glycogen has a molecular weight of 5-6 million and sometimes as much as 20 million (Iwanami Seibutsugaku Jiten [Dictionary of Biology], 4th Ed., p. 354, Iwanami-shoten (Tokyo) published on Mar. 21, 1996).

While glycogen is an animal storage polysaccharide, the glycogen is known to have an action of enhancing liver function. It was reported that a glycogen extracted from cuttlefish and scallops has a potent anti-tumor activity (Yosiaki Takata, et al., J. Mar. Biotech., 6. pp. 208-213 (1998)). Such a glycogen is useful as a novel material for functional foods and its applications have been developed.

Glycogen is biosynthesized from monosaccharides, such as glucose or the like, in the animal body.

In general, a polysaccharide sugar chain is synthesized by a chemical method or an enzymatic method. Both the methods are based on the principle that the OH group at an anomer position, which is to form a sugar hemiacetal ring, is previously activated as a leaving group and is subsequently replaced with another sugar or a biological component. To date, sialyl Le$^x$ ganglioside (contributing to the epoch-making result of researches on cell adhesion molecules or cancer-related antigens), calicheamicins (having a carcinostatic action), and the like have been developed using the chemical method, and cyclodextrins (having an inclusion action), coupling sugars (sweeteners substituting for sucrose, which are less responsible for tooth decay), and the like have been developed using the enzymatic method.

In the chemical method for synthesis of polysaccharide sugar chains, for example, it is known that a long chain oligosaccharide is degraded with acids; and various resultant monosaccharides are treated with a dilute acid, resulting in the reverse reaction in which a mixture of oligosaccharides are produced. In the enzymatic method, it is known that when sucrose is treated with invertase, which is a sugar hydrolytic enzyme, at a high concentration and high temperature, fructose is transferred to glucose, with 1 to 3 fructose molecules per one sucrose molecule to produce a fructooligosaccharide.

In general, chemical synthesis of polysaccharide sugar chains requires sugar donors, sugar acceptors, and promoters. Further, the sugar donors and the sugar acceptor or optionally their derivatives have to be prepared; and factors, such as solvents, dehydrators, temperatures, and the like have to be determined stringently. Furthermore, complicated steps, such as conversion or elimination of protecting groups, liberation of a specific hydroxyl group, or the like, are required. Therefore, it is not easy to chemically synthesize polysaccharide sugar chains. The sugar donors and the sugar acceptors as well as the factors have to be determined separately for each different substrate. There was no known technique for synthesis of sugar chains which can be generally applied to various substrate materials irrespective of their types.

SUMMARY OF THE INVENTION

The present inventors have diligently studied a synthesis method of polysaccharides. As a result, it was found that glycogen can be produced by heating and pressuring plants containing storage polysaccharides or polysaccharides themselves in the presence of acid. Thus, the present invention was completed. According to the present invention, a large amount of glycogen can be obtained by simple operations using plants containing a large amount of polysaccharides (e.g., starch and the like) as well as materials, such as starch, pullulan, cellulose, glucomannan, xylan, dextran, and the like. The present inventors further analyzed the physical properties of the obtained glycogens, leading to completion of the present invention. According to the present invention, glycogens, particularly a glycogen having a low molecular weight of 10,000 or less is provided.

The present inventors previously disclosed a two-step extraction method (Japanese Patent Application No. 2001-280812 entitled "Hyomenkoshitsu-no-Kokeibutsu-karano-Yukoseibun-no-Tyusyutsuho-oyobi -Denshitinganyusy-okuyoso-seibutsu [Method of Extracting Effective Components from Solid Substance with Hard Surface and Dencichine containing Composition for Foods" filed on Sep. 14, 2001), in which Panax notoginseng is pressure-treated in an organic acid solution so that cells in the skin portion thereof are destroyed and minerals are extracted from the Panax notoginseng, and subsequently, organic components are extracted from extract residue with a dilute ethanol solution, and further revealed that water-soluble Panax notoginseng extract powder containing a high concentration of both inorganic and organic components can be obtained. This Panax notoginseng extract powder contained about 86% glycosubstances. Note that "%" as used herein means percent by weight unless otherwise specified.

The present inventors do not consider that such a high sugar content and the anti-hepatitis action of Panax notoginseng are ascribed only to ginsenoside compounds, though they do not wish to be bound by any specific theory. The present inventors have diligently studied sugars which are present in the Panax notoginseng extract powder, and confirmed that one of the sugars is glycogen which is involved in an action of enhancing liver function. The present inventors quantitated the glycogen, resulting in completion of the present invention.

As a result, the Panax notoginseng extract powder contains about 37.45% (about 29.15% relative to the weight of the material) glycogen which is contained at only about 4.42% in Panax notoginseng itself. The glycogen was purified from the Panax notoginseng extract and was confirmed to be really glycogen by NMR measurement. In the course of purification of glycogen, it was confirmed that glycogens having various molecular weights were produced. Based on these findings, the present inventors considered that acids and pressure operations caused a transglycosylation reaction of sugar components to produce glycogens.

The present invention relates to a method of producing glycogen. The method comprises the step of heat- and pressure-treating a sugar-containing material under acidic conditions.

The sugar-containing material may be a polysaccharide or an oligosaccharide.

The sugar-containing material may be a homopolysaccharide of glucose.

The sugar-containing material may be starch, cellulose, pullulan, or dextran.

The sugar-containing material may be a plant material selected from the group consisting of Panax notoginseng, Yun Nan San-chi powder (trademark), Panax ginseng, wheat flour, soy bean, soy flour, shiitake, and coffee extract residue.

The plant material may be in the form of unprocessed tissue, granules or powder of a plant.

Preferably, the heating step is carried out in the presence of organic acid.

Preferably, the organic acid is citric acid.

Preferably, the heating step is carried out in the presence of citric acid having a weight of about 10% relative to the weight of the sugar-containing material.

Preferably, the heating step is carried out under pressure.

The present invention also relates to a plant extract containing glycogen derived from a plant. The plant extract may be prepared by a method comprising the step of heat- and pressure-treating a plant material under acidic conditions.

The method may further comprise the steps of separating an extract solution obtained by the step of heating- and pressure-treating the plant material under acidic conditions from an extract residue, and extracting the extract solution or the extract residue using an organic solvent.

Representatively, the above-described plant extract contains a high concentration of plant-derived glycogen. The plant extract is prepared as follows. A plant in its original form (hereinafter referred to as "unprocessed form", or the whole or a part of a plant in its original form is hereinafter referred to as "unprocessed tissue") or in the form of granules or powder is heated in an acidic solution for a predetermined time, followed by pressure- and heat-treatments. The resultant extract solution is combined with an extract solution obtained by subjecting the solid matter obtained as a residue to heat-extraction with about 40 to about 60% ethanol, followed by condensation. The resultant plant extract may be powdered into an extract powder form.

Representatively, the above-described acidic condition is achieved by addition of organic acid. pH 6 or less is preferable. Preferably, the organic acid may be citric acid. Note that the term "plant-derived glycogen" as used herein refers to glycogen contained in plants (root, stem and leaf) or glycogen produced from sugars contained in plants. The term "plant material" as used herein refers to plants (root, stem and leaf); portions thereof in any form obtained by a process, such as cutting, pulverizing, or the like (particles, slices, or the like); extracts from the whole or a part of plants; or the like.

The present invention also relates to a glycogen having a molecular weight of 10,000 or less.

Representatively, the glycogen has a molecular weight of about 3,000, about 9,000, or about 9,500.

The present invention also relates to a composition, comprising a glycogen having a molecular weight of 10,000 or less as a major component.

The composition may comprise a glycogen having a molecular weight of about 320,000 and a glycogen having a molecular weight of about 3,000.

The composition may comprise a glycogen having a specific rotation of $[\alpha]_D+197°$ and anomeric proton peaks at 5.37 ppm and 4.95 to 5.33 ppm in $^1$H NMR spectra.

The composition may comprise a glycogen having a molecular weight of about 280,000 and a glycogen having a molecular weight of about 9,000.

The composition may comprise a glycogen having a specific rotation of $[\alpha]_D+178°$ and anomeric proton peaks at 4.97 ppm and 5.22 to 5.33 ppm in $^1$H NMR spectra.

The composition may comprise a glycogen having a molecular weight of about 3,000,000, a glycogen having a molecular weight of about 1,200,000, and a glycogen having a molecular weight of about 9,500.

The composition may comprise a glycogen having a specific rotation of $[\alpha]_D+174°$ and anomeric proton peaks at 5.38 ppm and 4.96 ppm in $^1$H NMR spectra.

The present invention also relates to an edible composition, comprising the above-described plant extract. The edible composition may be prepared by incorporating the above-described plant extract or extract powder as a glycogen component.

BRIEF DESCRIPTION OF THE DRAWINGS

FIG. 3A(a) is a diagram showing the NMR spectra of a Panax notoginseng-derived purified glycogen contained in a composition of the present invention. FIG. 3A(b) is a diagram showing the NMR spectra of a standard glycogen.

FIG. 3B(c) is a diagram showing the NMR spectra of a dextran-derived purified glycogen contained in a composition of the present invention. FIG. 3B(d) is a diagram showing the NMR spectra of a starch-derived glycogen.

DETAILED DESCRIPTION

Figure 1:
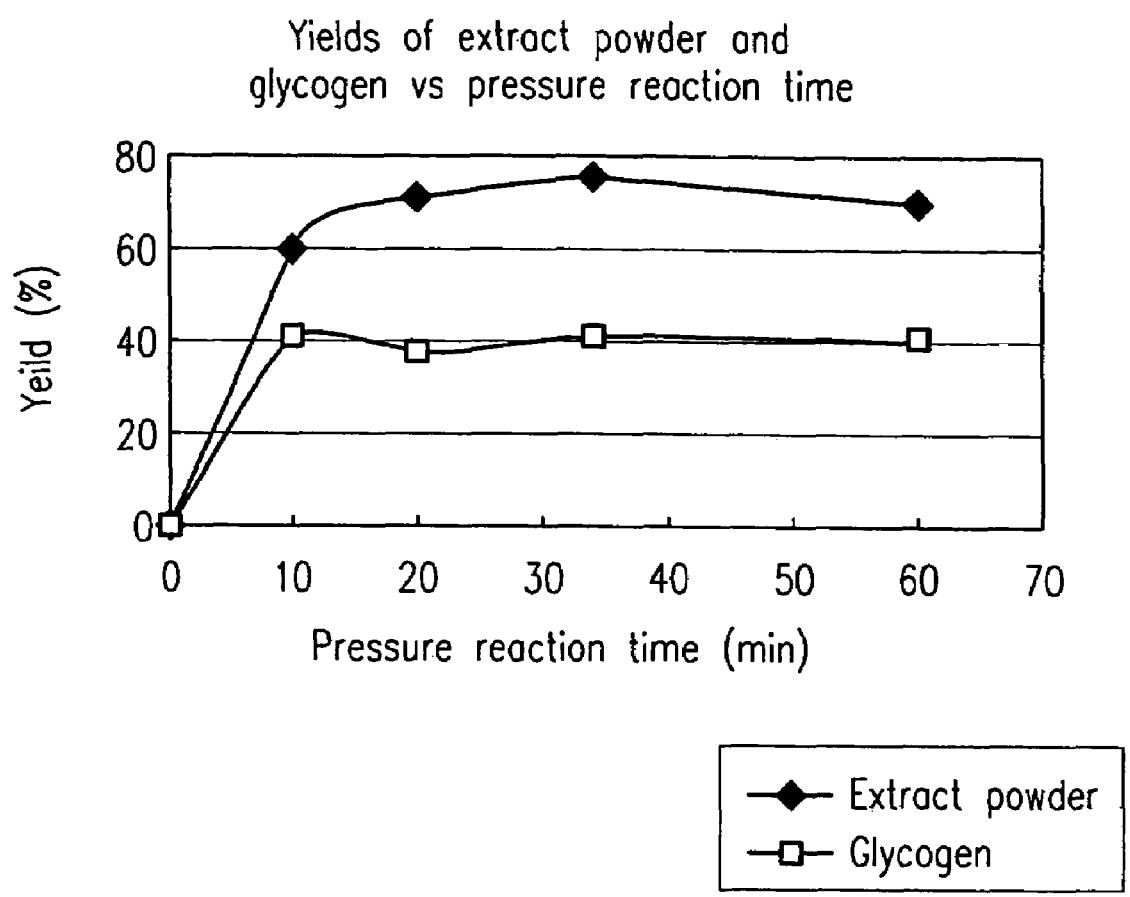
FIG. 1 is a diagram showing a yield over time of glycogen according to the present invention.

Hereinafter, embodiments of the present invention will be described in detail.

A sugar-containing material, which is a starting material for a glycogen of the present invention, typically includes polysaccharides, such as starch, cellulose, dextran, pullulan, and the like, and oligosaccharides, such as maltose and the like. A naturally-occurring plant material containing sugars, such as Panax notoginseng and the like, may be used as a sugar-containing material. Panax notoginseng contains ginsenoside, minerals and vitamins at high concentrations and may be used in any form of the unprocessed tissue and the pulverized fine particles, microparticles and fine powder, irrespective of the area of production and the time of harvest, as a starting material for a glycogen of the present invention.

A glycogen of the present invention is produced by a method comprising heat- and pressure-treating the above-described sugar-containing material under acidic conditions.

The above-described acidic conditions may be achieved by addition of an inorganic acid, such as phosphoric acid, hydrochloric acid, or the like. Alternatively, the acidic conditions may be achieved by using citric acid, acetic acid, lactic acid, tartaric acid, malic acid, lactic acid, succinic acid, gluconic acid and glucuronic acid, and sodium or potassium salts of these organic acids, and mixtures thereof. The acetic acid may be an edible acetic acid (synthetic vinegar, and fermented vinegars, such as apple cider vinegar, fruit vinegar, kelp vinegar, wine vinegar, and the like, and mixtures thereof in any proportion). More preferably, the acidic conditions may be achieved by using citric acid and acetic acid. Most preferably, the acidic conditions may be achieved by using citric acid.

A sufficient amount of the above-described inorganic or organic acid is added to the extent such that an aqueous solution containing the sugar-containing material has a pH of 6 or less and preferably a pH of 5 to 1, or typically is in the range of 0.1 to 20 wt %, more preferably 1 to 15 wt %, and most preferably 5 to 10 wt % relative to a sugar-containing material. Typically, an acid to be added to a sugar-containing material is diluted in water having a volume 2 to 15 fold, preferably 8 to 10 fold, greater than the sugar-containing material before adding the acid to the sugar-containing material.

The step of heat-treating the sugar-containing material under acidic conditions is carried out under atmospheric pressure at about 100° C. for, typically, 10 minutes to several hours, preferably 30 minutes to 2 hours. Alternatively, this heating step may be carried out under a pressure of 1 to 1.3 kgf/cm$^2$ at 75° C. to 125° C. (depending on the vessel). In this case, optionally, the acid-containing solution having the sugar-containing material may be preliminarily heated under atmospheric pressure at about 100° C. for, typically, 10 minutes to several hours, preferably 30 minutes to 2 hours before heating under pressure, thereby increasing the efficiency of production of glycogen.

A method of producing a glycogen according to the present invention may further comprise separating a solution containing a glycogen from a heated sugar-containing material. This step of separating the glycogen-containing solution may be carried out by a method known in the art, such as filtration, centrifugation, or the like. The obtained glycogen-containing solution may be condensed and dried by a method known in the art, such as freeze drying, spray drying, or the like, to obtain glycogen-containing powder.

Optionally, a glycogen of the present invention may be used after being further purified from the glycogen-containing powder. Purification of a glycogen may be carried out by a method well known in the art. For example, see Kazuo Matsuda, ed., "Tato-no-Bunri-Seiseiho [Method for Separation and Purification of Polysaccharide]", pp. 130-131, 1989. Such a method includes fractional precipitation using alcohol. Representatively, the alcohol includes methanol and ethanol. Optionally, the glycogen-containing powder may be subjected to deproteinization or the like before the above-described processes. Such deproteinization includes trichloroacetic acid treatment, treatment using a solvent, such as alcohol, chloroform or the like, which are known in the art. For the purified glycogen, known methods, such as gel filtration, specific rotation, an NMR measurement test, and the like, may be used to identify the physical properties, such as molecular weight, molecular weight distribution, glucose linkage type, and the like, and analyze the structure.

A representative exemplary method of efficiently producing a glycogen-containing powder according to the present invention will be described below.

Appropriately granulated Panax notoginseng is heated in 10 wt % citric acid aqueous solution at 90 to 100° C. for 1 hour while optionally stirring. Thereafter, the solution is pressure- and heat-treated for two hours after starting pressurization while keeping 1.1 to 1.3 kgf/cm$^2$, followed by separation of an extract solution from a solid fraction extract residue in accordance with a commonly used method, such as filtration or the like. The obtained extract solution is subjected to drying (freeze drying, spray. drying, or the like) to obtain a glycogen-containing powder of the present invention. Note that Panax notoginseng may be used in any form of unprocessed tissue, fine granules, and powder.

In the above-described examples, Panax notoginseng is used as a sugar-containing material. The present invention is not so limited and can be implemented where plant materials, such as wheat flour, soybean, Panax ginseng, Zinsic, turmeric, and the like, are used as sugar-containing materials instead of Panax notoginseng. Also in this case, glycosubstances contained in these plant materials can be converted to glycogen without impairing effective components contained in the materials and respective glycogen-containing powders can be obtained. In a method of producing glycogen according to the present invention, sugars themselves, such as polysaccharides, oligosaccharides, and the like, can be used as starting materials instead of the above-described plant materials. It will be appreciated that the present invention is not limited to the above-described sugar-containing materials.

The glycogen-containing powder of the present invention is particularly characterized in that it is highly water soluble. Therefore, the powder can be applied to food compositions in a liquid, gel or solid form without limiting the type thereof. For example, the powder may be added to soft drinks, juices, teas, jellies, puddings, breads, cookies, caramels, Okaki (Rice cookies), and the like. The powder can be processed into powders, granules, or tablets optionally along with excipients, such as starch, dextrin, lactose, or the like, and other edible compositions, such as extracts, pigments, flavorings, or the like, or alternatively, can be encapsulated with a coating agent, such as gelatin or the like. The resultant products can be used as health foods, dietary supplements, and the like. It will be appreciated that edible composition applications of the glycogen-containing powder of the present invention are not limited to the above-described examples.

The glycogen-containing powder content of the edible composition may be in the range of about 0.1 to 100 wt % depending on the type, condition or the like of the edible composition.

The glycogen-containing powder of the present invention can be easily mixed with other substances in an adjustable manner such that the powder highly effectively serves as a functional factor. This is because effective components of plant materials are extracted in a water soluble form.

Hereinafter, the present invention will be described by way of examples. The following examples are for purposes of illustration, by which it is not intended to limit the present invention.

EXAMPLES

Example 1

Preparation of Panax Notoginseng Extract 91 kg of granules (2 to 3 mmφ) of Panax notoginseng, 9 kg of citric acid and 550 L of water were placed in a tank with a pressure device, followed by heating at 90 to 96° C. for one hour. Thereafter, the mixture was kept under a pressure of 1.1 kgf/cm$^2$ for one hour. The resultant reaction solution was subjected to filtration using a pressure filtration apparatus having NA500 filter paper. The resultant extract solution was aliquoted. Thereafter, 700 L of 45 wt % ethanol solution was added to the Panax notoginseng extract residue, followed by heating with reflux at 65° C. for 2 hours. The resultant reaction solution was subjected to filtration using a pressure filtration apparatus having NA500 filter paper and the ethanol extract solution was aliquoted. The thus-obtained citric acid extract solution and ethanol extract solution were mixed together and condensed. The resultant condensed solution was subjected to spray drying, resulting in 65.76 kg of extract powder (freeze dried powder). Components contained in the extract powder were analyzed. The results of the measurement are shown in Table 1.

As shown in a) in Table 1, the obtained Panax notoginseng extract powder contained 37.45% glycogen. Note that glycogen was measured in accordance with the oyster extract foods standards (Japan Health Food & Nutrition Food Association); in Table 1, the glycogen concentration (%) is represented by the glycogen content of the extract powder obtained by freeze drying in units of wt %, and the glycogen production rate is represented by the weight of glycogen contained in the extract powder divided by the weight of the starting material (a calculated value relative to the weight of the material).

Table 1-a) shows the results of measurement of glycogen contained in Yun Nan San-chi powder (trademark) extract powder, Panax ginseng unprocessed tissue extract powder, wheat flour extract powder, soy bean unprocessed tissue extract powder, soy flour extract powder, and shiitake (*Lentinula*) extract powder, which were similarly obtained as shown in Example 4 below, except that 10 to 30 g extract powder was used. As shown in Table 1-a), Yun Nan San-chi powder (trademark) extract powder, Panax ginseng unprocessed tissue extract powder, wheat flour extract powder, soy bean unprocessed tissue extract powder, soy flour extract powder, and shiitake extract powder contained 32.70 wt %, 18.29 wt %, 47.06 wt %, 5.82 wt %, 44.03 wt %, and 1.74 wt % glycogen, respectively. The results shown in Table 1-b) will be described in Example 4 below.

TABLE 1 a)

Glycogen produced from plants by a method of the present invention

| Samples | Glycogen concentration in FD* powder ($) | Glycogen production rate per material (%) |
|---|---|---|
| *Panax notoginseng* powder | — | (4.42) |
| *Panax notoginseng* extract powder | 37.45 | 29.15 |
| Yun Nan San-chi powder (trademark) | — | (1.51) |
| Yun Nan San-chi powder (trademark) extract powder | 32.70 | 20.05 |
| *Panax ginseng* unprocessed tissue extract powder | 18.29 | 5.49 |
| Wheat flour extract powder | 47.06 | 32.70 |
| Soy bean unprocessed tissue extract powder | 5.82 | 1.60 |
| Soy flour | — | (0.47) |
| Soy flour extract powder | 44.03 | 2.02 |
| Shiitake | — | (0.15) |
| Shiitake extract powder | 1.74 | 0.75 |
| *Ganoderma lucidum* | — | (2.55) |
| *Ganoderma lucidum* extract powder | 2.28 | 0.87 |
| *Agaricus* extract powder*[1] | — | (32.53) |
| | 1.67 | 0.87 |

TABLE 1 a)-continued

Glycogen produced from plants by a method of the present invention

| Samples | Glycogen concentration in FD* powder ($) | Glycogen production rate per material (%) |
|---|---|---|
| *Agaricus* extract powder Coffee extract residue | 8.64 | —*[2] |

*FD represents Freeze dry. Parenthesized values represent the original glycogen content of plants.
*[1]Extraction was carried out at 125° C. using hot water under pressure.
*[2]No result was available, since the water content of coffee extract residue was unclear.

TABLE 1b)

| Samples | Quantitative value of glycogen (%) |
|---|---|
| Pien Tze Huang (for domestic) | 3.49 |
| Pien Tze Huang (for export) | 2.65 |

(Example 2) Study on Conditions for Production of Glycogen 175 mL of water, 30 to 35 g of Panax notoginseng unprocessed tissue, and citric acid corresponding to 9 wt % of the Panax notoginseng unprocessed tissue were added to each of four Erlenmeyer flask, which were in turn covered with food wrapping film, followed by boiling under a pressure of 1.1 to 1.2 kgf/cm$^2$ for 10 min, 20 min, 35 min, and 60 min, respectively, in an autoclave. Each reaction product was allowed to cool. The solution portion of the reaction product was centrifuged (3,000 rpm, 5 min) to obtain an extract solution. Precipitation residue was returned to the Erlenmeyer flask still containing the original Panax notoginseng unprocessed tissue. 200 mL of 50% ethanol solution was added to the flask, which was in turn fitted with a reflux condenser, and the solution was heated at 85° C. for 1 to 1.5 hours. The resultant heated solution was allowed to cool, followed by centrifugation (5,000 rpm, 10 min). The ethanol extraction solution was aliquoted and was then mixed with the previously aliquoted extract solution, followed by condensation under reduced pressure and then freeze drying, resulting in powder.

The production amount and glycogen content of the resultant extract powder were measured and the results are shown in FIG. 1. As shown in FIG. 1, the yield of the extract powder was the highest, 74%, at 35 min in the pressure time, and the glycogen production rate reached about 40% at 10 min and subsequently was almost constant until 60 min. Therefore, it was judged that 35 min is sufficient for the pressure time under a pressure of 1.1 to 1.2 kgf/cm$^2$.

Example 3

Glycogen production rates were compared by varying citric acid concentration under the pressure conditions obtained in Example 2 (i.e., 1.1 to 1.2 kgf/cm$^2$, 35 min). The same procedure as that of Example 2 was carried out, except that the citric acid concentration was changed to 5, 6, 7, 8 and 9% relative to the material. The results are shown in Table 2. As shown in Table 2, in the case of the 9% citric acid addition, the glycogen production rate was the highest 41.4%. Next, glycogen production rates were compared by varying pressure time.

TABLE 2

Dependence of glycogen production on citric acid concentration

| Citric acid addition concentration relative to material | Glycogen production rate (%) | Extract amount (%) |
|---|---|---|
| 9% | 41.4 | 74.0 |
| 8% | 38.3 | 72.3 |
| 7% | 35.6 | 68.9 |
| 6% | 29.1 | 66.6 |
| 5% | 30.9 | 63.2 |

Example 4

Samples other than Panax notoginseng were subjected to extraction under pressure conditions similar to those of Example 2 so as to study glycogen production by the extraction method of the present invention.

10 to 30 g of Yun Nan San-chi powder (trademark), Yun Nan San-chi powder (trademark) extract powder, Panax ginseng unprocessed tissue extract powder, wheat flour extract powder, soy bean unprocessed tissue extract powder, soy flour, soy flour extract powder, shiitake, shiitake extract powder, *Ganoderma lucidum*, *Ganoderma lucidum* extract powder and coffee extract residue were treated under pressure conditions (1.1 to 1.2 kgf/cm$^2$, 35 min) in a manner similar to that of Example 2. Eventually, freeze dried powder was obtained and the glycogen content thereof was measured. The results are shown in Table 1 above.

As shown in Table 1-a), the Panax notoginseng extract powder contained about 29.15% (relative to the weight of the material) glycogen which is contained at only about 4.42% in Panax notoginseng itself. Thus, the glycogen content was increased by a factor of 6.5 or more by the pressure treatment of the present invention. Similarly, for "Yun Nan San-chi powder" (trademark), which is made of Panax notoginseng and contains 1.51% glycogen, the extract powder obtained by the extraction method of the present invention contained 20.05% glycogen, i.e., the glycogen content was increased by a factor of 13.3.

The glycogen contents of extract powders made of dried Panax ginseng unprocessed tissue, which belongs to the same genus as that of Panax notoginseng, and dried soy bean unprocessed tissue, were 5.49% and 1.60% relative to the weight of the material, respectively. These values are smaller by one or more orders of magnitude than that of Panax notoginseng. The glycogen content of wheat flour extract powder was 32.78% relative to the weight of the material.

The glycogen contents of soy flour and soy flour extract powder made of soy bean were 0.47% and 2.02% relative to the weight of the material, respectively. Thus, the glycogen content was increased by a factor of about 4.3 by the extraction method of the present invention.

The glycogen contents of shiitake included among mushrooms and extract powder thereof were 0.15% and 0.75% relative to the weight of the material, respectively. Thus, the glycogen content was increased by a factor of about 5 by the extraction method of the present invention.

The glycogen content of coffee extract residue extract powder was 8.64% relative to the weight of the extract powder.

In contrast, the glycogen contents of *Ganoderma lucidum* and *Agaricus* were reduced from the original contents by the extraction method of the present invention.

The above-described results revealed that a large amount of plant-derived glycogen can be produced from plants by a physicochemical method comprising heating and pressuring in the presence of acid. Among mushrooms, shiitake contains lentinan which is β-glucan having an anti-tumor activity, and *Agaricus* also contains β-glucan having an anti-tumor activity. By the method of the present invention, a significant difference was recognized between shiitake and *Agaricus* such that glycogen was increased in the case of shiitake while glycogen was decreased in the case of *Agaricus*. This is a noteworthy result.

Note that Pien Tze Huang shown in Table 1-b) is a Chinese medicine containing 85% Panax notoginseng. Pien Tze Huang contained about 3% glycogen which is not different from the glycogen content of Panax notoginseng itself.

Example 5

In order to confirm an increase in glycogen content due to glycogen production when a material derived from a plant is subjected to the extraction method of the present invention, various sugars were used as materials and were treated in a manner similar to that of Example 2, and the glycogen contents were measured. The results are shown in Table 3.

TABLE 3 a) Production of glycogen from various monosaccharides, oligosaccharides and polysaccharides by the method of the present invention

| Samples | Glycogen production rate (%) |
|---|---|
| Potato starch (insoluble) | 23.04 |
| Maize starch (insoluble) | 12.02 |
| Soluble starch | 0.82 |
| Cellulose | 0.65 |
| Pullulan | 36.78 |
| Dextran | 71.26 |
| (dextran top layer soluble) | (32.60) |
| (dextran bottom layer soluble) | (39.66) |
| Raffinose | 0.39 |
| Maltose | 0.28 |
| Trehalose | 0 |
| Sucrose | 0 |
| Glucose | 0 | b)

| Samples | Quantitative value of glycogen (%) |
|---|---|
| Standard glycogen (Wako Pure Chemical Industries, Ltd.) | 79.99 |
| Standard glycogen (Sigma, oyster glycogen) | 51.24 |

As a material, starch, which is contained in a large amount in seeds, roots, rhizomes, and the like of higher plants, was used. Starch is a polysaccharide consisting of D-glucose i) Potato starch: A sample of potato starch with citric acid and a sample of potato starch without citric acid were prepared. The samples were obtained in the form of cloudy aqueous solution having white insoluble matter. The samples were pressure-treated at 1.1 kfg/cm$^2$ for 35 min, so that the sample with citric acid was a runny solution without insoluble matter, while the sample without citric acid was transparent but insoluble matter remained. Therefore, the sample without citric acid was centrifuged to remove the remaining insoluble matter, resulting in a transparent sample solution.

For the sample with citric acid in which insoluble matter remained, ethanol was added to the reaction solution to a concentration of 45%. For the sample without citric acid, 45% ethanol was added to the separated insoluble matter. Each sample was heated for one hour. For the sample with citric acid, slight precipitation was recognized in the obtained reaction solution, while for the sample without citric acid, silk-like precipitate was produced. The solutions from which these precipitates were removed were mixed with the respective reaction solutions previously obtained after the pressure treatment, followed by condensation and freeze drying. The glycogen content of the resultant powder was measured.

As a result, a large amount of glycogen reaching 23.04% was found from potato starch according to the method of the present invention. In the case of the control sample without citric acid, no glycogen was recognized in the freeze dried powder as shown in Table 3.

ii) Maize starch: For maize starch, a sample with citric acid and a sample without citric acid were prepared, similar to potato starch. After a pressure reaction, the samples both were turned to gel, so that the solution portion could not be separated from the precipitate. Ethanol was directly added to each sample to 45%, followed by heating for one hour. As a result, for the sample with citric acid, powdery insoluble matter was obtained, and was separated and removed by filtration to obtain the solution portion. For the sample without citric acid, continuous cloth-like insoluble matter was produced. The insoluble matter was wound around a glass rod and removed, resulting in a transparent solution portion. Each solution portion was condensed to a predetermined amount, followed by freeze drying, resulting in extract powder. Glycogen in the resultant extract powder was quantitated. As a result, whereas no glycogen was found in the extract powder of the sample without citric acid, 12.02% glycogen was recognized in the sample with citric acid.

iii) Soluble starch: As shown in Table 3, 0.82% glycogen was produced from soluble starch by the extraction method of the present invention.

iv) Cellulose, pullulan and dextran: 0.65%, 36.78% and 71.26% glycogens were produced from cellulose, pullulan and dextran by the extraction method of the present invention. In the case of dextran, a reaction solution was separated into two layers both after pressure treatment and after addition of 45% ethanol solution followed by heating. Therefore, the top layer portion and the bottom layer portion of the solution were separated from each other. Each portion was condensed, followed by freeze drying. Thus, the freeze dried powder was obtained. The freeze dried powders from the top layer portion and the bottom layer portion contained 32.60% and 38.66% glycogen, respectively, i.e., a total of 71.26% glycogen was obtained.

v) Raffinose, maltose, trehalose, sucrose, and glucose: On the other hand, when raffinose (trisaccharide), maltose, trehalose and sucrose (disaccharide), and glucose (monosaccharide) were used, 0.39% and 0.28% glycogens are recognized for raffinose and maltose according to the extraction method of the present invention. When trehalose, sucrose and glucose were used as materials, glycogen was not detected.

When the disaccharides were used as materials, the presence or absence of glycogen generation was ascribed to the fact that maltose is a reducing sugar while trehalose and sucrose are non-reducing sugars. When trehalose and sucrose were used as materials, a polysaccharide other than glycogen was inferred to be produced. Thus, it was considered to be difficult to form a polysaccharide using glucose.

As described above, even when the extraction method of the present invention was applied to polysaccharides, glycogen production was recognized. Thus, it was confirmed that plant-derived glycogen can be produced from plants by a physicochemical method in the presence of acids.

For example, it is inferred that when a mixture of Panax notoginseng and dextran are used as a material, glycogen is produced having a structure different from that which is generated when each material is separately used. A novel business such that glycogen is produced from mannan which is contained in coffee extract residue, may be expected, for example.

Example 6

50% oyster extract, 28.9% Panax notoginseng extract powder obtained under conditions similar to those of Example 2, and 3% lubriwax were mixed and subjected to sieve analysis. To the resultant mixture was added 20% lactose, 1% calcium triphosphate, and 2.0% sucrose fatty ester, followed by thorough mixing. The resultant mixture was tableted, followed by shellac coating and polishing, to produce a prototype edible composition tablet.

Example 7

62.5% Panax notoginseng extract powder obtained under conditions similar to those of Example 2 and 12.2% multitol were preliminarily mixed, followed by addition of 0.5% pullulan, to produce preliminary granules (containing 1 to 2% moisture). To this preliminary granule were added 16.8% fermented turmeric and 8% lubriwax while premixing, followed by thorough mixing. The mixture was tableted. The tablet was coated with yeast wrap and glycerin to produce a prototype edible composition.

Example 8

The equivalents of 10.0 wt % vitamin E, 6.6 wt % maltose, and 1.6 wt % calcium phosphate were mixed using a mixer to produce a preliminary mixture powder. This powder was thoroughly mixed with 20.9 wt % Panax notoginseng extract powder obtained in a manner similar to that of Example 2, 10 wt % starch, and 45 wt % lactose-powder cellulose, followed by sieve analysis. The mixture was placed into a mixer, and 5 wt % sucrose fatty ester, 0.9 wt % calcium phosphate, and 5 wt % lactose-powder cellulose was added to the mixture, followed by mixing. The resultant powder was tableted, followed by shellac coating and polishing, to produce a prototype edible composition tablet.

Example 9

48.99 wt % Panax notoginseng extract powder obtained in a manner similar to that of Example 2, 8.6 wt % vitamin C, 0.12 wt % vitamin B6 hydrochloride, 5 wt % sucrose ester, and 6.04 wt % crystalline cellulose were mixed. This mixture was mixed with 31.25 wt % reducing maltose aqueous solution, followed by tableting. Shellac 10 wt % ethanol solution was prepared in an amount of 7 to 8% relative to the tablet. This solution was sprayed onto the tablet for the purpose of shellac coating to produce a prototype edible composition.

Example 10

Preparation of Purified Glycogen

1. Preparation of purified glycogen from potato starch and dextran

When attempting to dissolve 20 g of glycogen-containing powder obtained from potato starch in a manner similar to that of Example 5 i) in 200 mL of purified water, the powder was completely dissolved. This colorless solution was heated at 95° C. for 20 min and was then allowed to cool at room temperature. Thereafter, the solution was cooled at 5° C. for 1.5 hours. The solution was recognized to be turned slightly cloudy. Therefore, the solution was centrifuged at 8,500 rpm for 6 min to remove the cloudy substance. The resultant supernatant was cooled at 5° C. Thereafter, trichloroacetic acid was added to the supernatant to a concentration of 5% and was allowed to stand at 5° C. overnight. Thereafter, precipitate was removed by centrifugation (8,500 rpm, 6 min). The resultant supernatant was added to a 3-fold volume of methanol. The resultant precipitate was collected by centrifugation (8,500 rpm, 10 min). The resultant precipitate was washed with methanol and ether successively. This precipitate was dried in a vacuum dryer at room temperature for 2 hours, resulting in crude glycogen.

20 g of the obtained crude glycogen was placed in a cellophane tube, followed by dialysis with respect to 1.4 to 1.5 L of purified water at 5° C. for 3 days. During this period of time, purified water was newly exchanged every day. Thereafter, the dialyzate was freeze dried. The resultant dried powder was obtained as purified glycogen.

Next, purified glycogen was similarly obtained from glycogen-containing powder obtained from dextran in a manner similar to that of Example 5 iv). The yield of the purified glycogen was 16.2% and 18.2% for potato starch and dextran, respectively.

The physical properties of the above-described purified glycogen specimens are shown in Table 4.

TABLE 4

| Physical properties | Glycogen derived sugar materials | | Standard substances | | |
|---|---|---|---|---|---|
| | Prnified glycogen derived from potato starch | Purified glycogen derived from dextran | Granulated sugar | Glucose | Glycogen (Wako Pure Chemical Industries) |
| Sugar content | 7.5% | 5.0% | 5.0% | 5.6% | 5.0% |
| Iodine reaction | Color change to magenta | Color change to magenta having slightly weaker red | Pale yellow | Light yellow | Light brown |
| Glycogen content | 50.8% | 60.0% | — | — | 79.99% |

Note that in Table 4, sugar content was measured by preparing a 5% solution of each specimen and determining the sugar content of the solution using a brix refractometer (manufactured by Atago). Iodine reaction was carried out using 0.01 mol/L iodine solution. Further, the glycogen content in the purified glycogen was measured in accordance with the oyster extract foods standards (Japan Health Food & Nutrition Food Association).

2. Preparation of Glycogen from Panax Notoginseng

When 30 g of glycogen-containing powder obtained from Panax notoginseng as described in Example 1 was dissolved in 300 mL of purified water, insoluble matter was generated. The insoluble matter was removed by centrifugation (8,500 rpm, 6 min, 10° C.) to obtain a brown supernatant. This supernatant was heated at 95° C. for 20 min and was allowed to cool at room temperature. Thereafter, the supernatant was cooled at 5° C. for 1.5 hours. The cloudiness of the solution increased. The cloudy components were removed by centrifugation at 8,500 rpm for 6 min to obtain a supernatant. This supernatant was cooled to 5° C. overnight. Trichloroacetic acid was added to the supernatant to a concentration of 5% and was allowed to stand at 5° C. Thereafter, centrifugation was carried out (8,500 rpm, 6 min) to remove precipitate. The resultant supernatant was added to a three-fold volume of methanol. The resultant pale brown precipitate was collected by centrifugation. The resultant precipitate was washed with methanol and was dissolved in about 200 mL of dimethylsulfoxide (DMSO). Insoluble matter was removed by centrifugation (6,500 rpm, 10 min, 10° C). To the resultant supernatant was added a three-fold volume of ethanol to carry out reprecipitation. This ethanol reprecipitation was carried out further two times for purification. Thereafter, purification was carried out by two times reprecipitations with purified water instead of DMSO. The resultant milk white precipitate was vacuum-dried at room temperature to obtain 24.7 g of dried powder. 20 g of this dried powder was dissolved in 140 mL of purified water, to which a mixture of 36 mL of iso-amyl alcohol and 108 mL of chloroform was added, followed by mildly shaking for 10 hours. This solution was allowed to stand. Thereafter, the resultant water layer was aliquoted, followed by centrifugation (7,500 rpm, 30 min, 10° C.). This protein-removing operation was carried out two times with addition of a mixture of 36 mL of iso-amyl alcohol and 108 mL of chloroform. Thereafter, the resultant a white to yellowish white solution was placed in a cellophane tube, followed by dialysis with respect to 1.4 to 1.5 L of purified water at 5° C. for 3 days. During this period of time, purified water was newly exchanged every day. Thereafter, the dialyzate was freeze dried to obtain 13.4 g of purified glycogen (the glycogen was 69.0% and the glycogen yield was 11.9%). This purified product exhibited a magenta color in an iodine reaction.

Example 11

Analysis of Purified Glycogen

1. Molecular Weight

The molecular weight of purified glycogen obtained in Example 10 was measured by gel filtration.

1.1. Preparation of Samples

Purified glycogens obtained from starch, dextran and Panax notoginseng were weighed into 3.16 mg, 3.32 mg and 3.33 mg samples, respectively. Each purified glycogen was dissolved in 1 mL of purified water, 50 μL of which was subjected to HPLC analysis.

1.2. HPLC Apparatus and Measurement Conditions Conditions for HPLC Analysis were the following.

Figure 2:
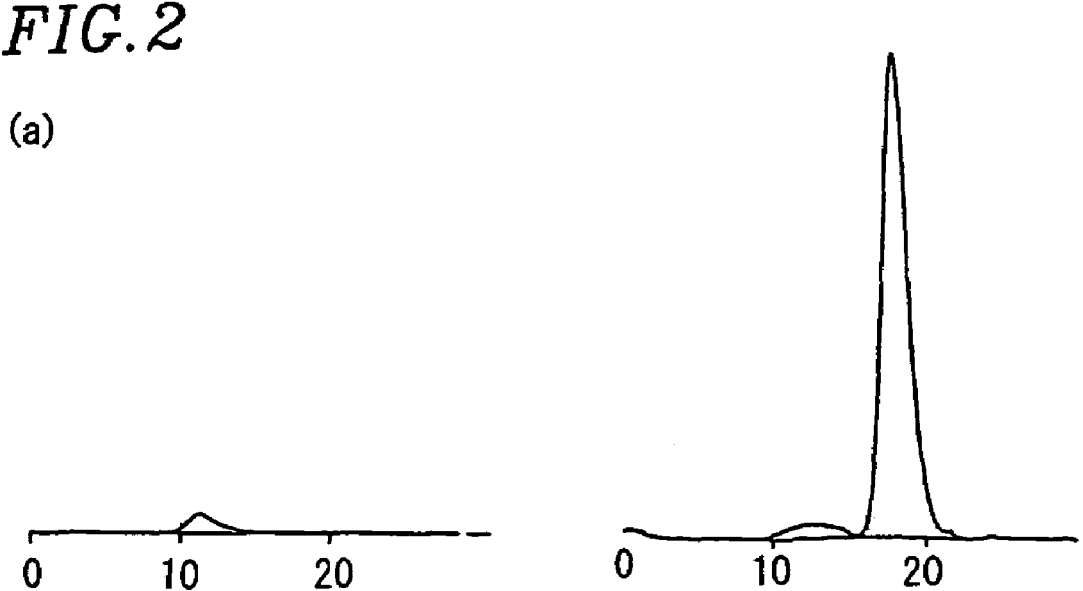
FIG. 2 is a diagram showing a chromatogram of HPLC analysis of a composition of the present invention.
Figure 2:
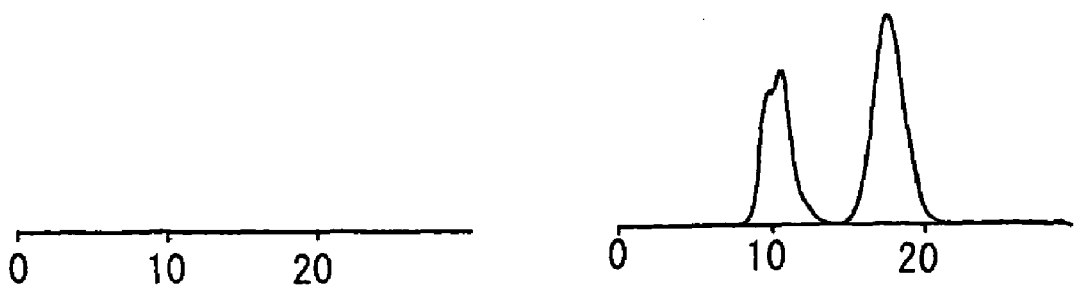
Figure 2:
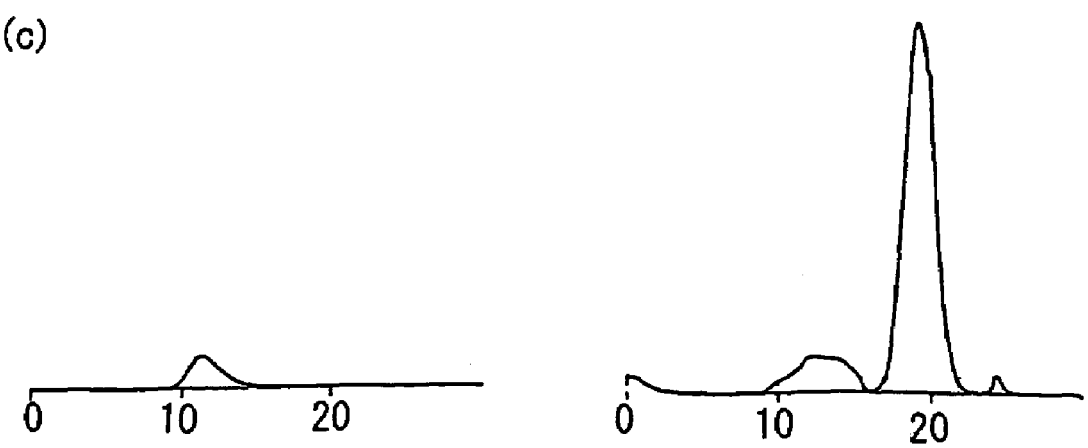

HPLC apparatus: LC-7A with IJV spectrophotometer detector SPD-6A (Shimazu Corporation). Column: Shodex Asahipak CS-620 (50 cm×7.6 mm I.D.) (manufactured by Showa Denko); Mobile phase: purified water; Mobile phase flow rate: 0.8 mL/min; Detection wavelength: UV 280 nm 1.3. Results Using a calibration curve, which had been prepared using pullulan and glucose oligomer as standard substances, the molecular weight of glycogen contained in each example was measured based on a retention time in HPLC analysis. FIG. 2 shows an exemplary chromatogram of HPLC analysis. In FIG. 2, (a) indicates a chromatogram of purified glycogen from dextran, (b) indicates a chromatogram of purified glycogen from Panax notoginseng, and (c) indicates a chromatogram of purified glycogen from glycogen. Note that each of (a), (b) and (c) of FIG. 2 shows the results of the same sample, where a left hand chromatogram indicates the results of measurements using the UV spectrophotometer detector while a right hand chromatogram indicates the results of measurement using a differential refractometer detector. As shown in FIG. 2, it was revealed that each sample is made of a plurality of molecular species having different molecular weights. The molecular weight of each molecular species and the proportion of each molecular species to the weight of the sample are shown in Table 5.

TABLE 5

| Physical property | Glycogen from sugar material | | |
|---|---|---|---|
| | Potato starch | Dextran | Panax notoginseng |
| Molecular weight (proportion) | 320,000 (14.4%) 3,000 (84.3%) <180 (1.3%) | 280,000 (4.9%) 9,000 (95.1%) | 3,000,000 (14.3%) 1,200,000 (25.1%) 9,500 (60.6%) |

As shown in Table 5, it was revealed that glycogen obtained from starch contained a molecule having a molecular weight of 3,000 as a major component; glycogen obtained from dextran contained a molecule having a molecular weight of 9,000 as a major component; and glycogen obtained from Panax notoginseng contained a molecule having a molecular weight of 9,500 (60.6%) as a major component.

As compared to the glycogen produced from Panax notoginseng, the glycogens produced from starch and dextran have a characteristic feature that they have a small molecular weight. According to literature (Seibutugaku-Jiten [Dictionary of Biology], Iwanami Syoten, supra), liver glycogen has a molecular weight of 5 to $10 \times 10^6$ and muscular glycogen has a molecular weight of 1 to $2 \times 10^6$. It was revealed that as compared to these values, the three purified glycogens all have a relatively low molecular weight.

2. Specific Rotation

Each purified glycogen obtained in Example 10 was precisely weighed into 0.1 g sample, to which purified water was added to 20 mL. Each sample solution was placed into a measurement tube having a vessel length of 200 mm. The specific rotation of each sample was measured using an optical rotatory meter (manufactured by Elmer).

As a result, the measurement value of the purified glycogens produced from starch, dextran and Panax notoginseng were $[\alpha]_D+197.2°$, $[\alpha]_D+178.4°$, and $[\alpha]_D+174.1°$, respectively.

According to literature (Seikagaku-Jiten [Dictionary of Biochemistry] (3rd Ed.), Tokyo Kagaku Dojin, p. 402, Oct. 8, 1998), the specific rotation of glycogen solution is $[\alpha]_D+191$ to $+200°$ (the specific rotation of starch is $[\alpha]_D+202°$). The purified glycogen solution from starch was the only solution to indicate the specific rotation within this range. The specific rotations of the purified glycogen solutions from Panax notoginseng and dextran were lower than the value described in the literature.

3. $^1$H NMR Measurement

Purified glycogen obtained in a manner similar to that of Example 10 was characterized by $^1$H NMR measurement. Glycogen is a homopolysaccharide made of glucose and can be identified by using a signal from an anomeric proton derived from glucose as an indicator. $^1$H NMR measurement was carried out as follows.

3.1. Preparation of Samples

Purified glycogen solutions from starch and dextran: for each, 11 mg/0.65 mL D$_2$O solution was prepared. A glycogen reagent (manufactured by Wako Pure Chemical Industries, Ltd.: standard substance) and purified glycogen derived from Panax notoginseng: for each, 10 mg/0.65 mL D$_2$0 solution was prepared.

3.2. Conditions for Measurement

UNITY INOVA 600 type apparatus (manufactured by Varian Corporation) was used under the following conditions.

Observation frequency 599.6 MHz; temperature 45° C.; observation width 6 KHz; pulse width 30°; and pulse repetition time 7 sec.

3.3. Results (1) Standard Substance

For the glycogen reagent (manufactured by Wako Pure Chemical Industries, Ltd.), anomeric proton peaks were observed around 5.39 ppm and around 4.98 ppm. An exemplary peak of anomeric proton is shown in FIG. 3A(b).

The peak at 5.39 ppm is attributed to α1-4 linkage. The peak at 4.98 ppm is attributed to α1-6 linkage. α1-6 linkage accounts for about 5%. A peak which was inferred to correspond to an impurity was observed at 1 to 3.3 ppm.

(2) Purified Glycogen from Panax Notoginseng

Figure 3A:
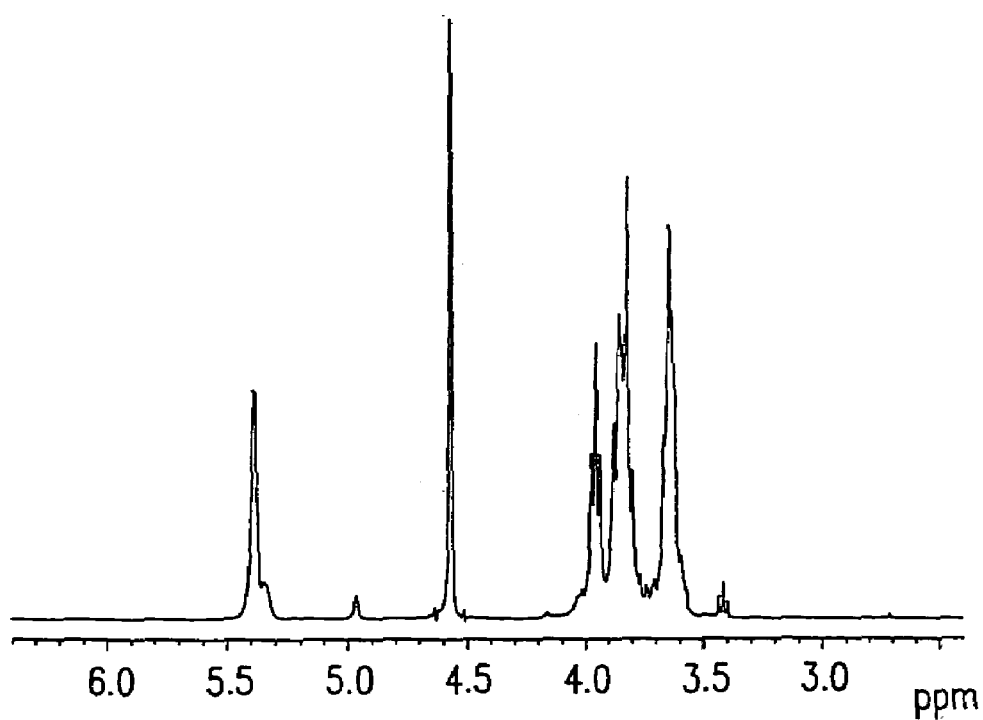
FIG. 3A shows diagrams showing the NMR spectra of glycogen contained in a composition of the present invention.
Figure 3A:
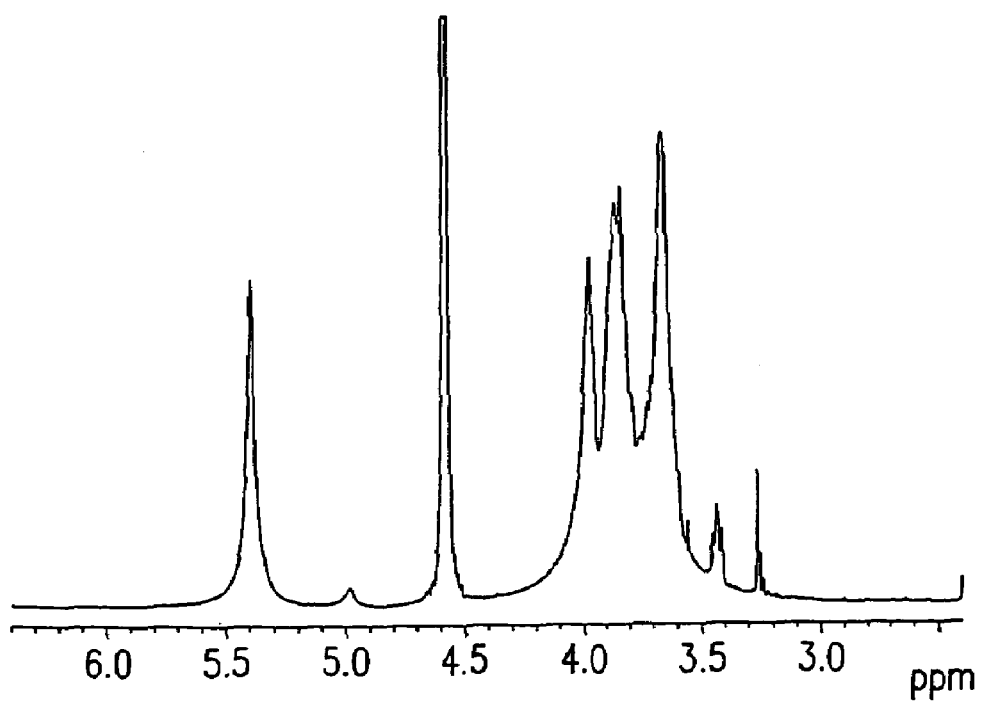

As shown in FIG. 3A(a), purified glycogen from Panax notoginseng extract powder obtained in section 2 of Example 10 had a 5.38 ppm anomeric proton peak corresponding to α1-4 linkage and a 4.96 ppm anomeric proton peak corresponding to α1-6 linkage, as did the standard glycogen (Wako Pure Chemical Industries, Ltd.) shown in FIG. 3A(b), and thus, was confirmed to be glycogen. Comparing the signal level ratio of anomeric proton at 5.38 ppm and 4.96 ppm between the purified glycogen from Panax notoginseng extract powder and the standard product, the ratio for the purified glycogen from Panax notoginseng extract powder was about 10:1 (70.9/7.1), and for the standard product, about 20:1 (80.2/4.4). It was suggested that the difference is ascribed to a difference in microstructure, such as the degree of branching in sugar chain structure, and the like, of the purified glycogen from Panax notoginseng extract powder and the standard product. Considering a report indicating the relationship between the microstructure and anti-tumor activity (Yosiaki Takata et al., J. Mar. Biotech., 6. pp. 208-213 (1998)), the microstructure difference was believed to be involved in the anti-tumor activity of Panax notoginseng. Peaks for the purified glycogen from Panax notoginseng, which were inferred to correspond to impurities, were present only at 1.2 ppm and 2.7 ppm, and it was thus indicated that the degree of purification thereof was high as compared to the standard product whose peaks inferred to correspond impurities were present at 1 to 3.3 ppm. α1-6 linkage accounts for about 10%.

(3) Purified Glycogen from Starch

Figure 3B:
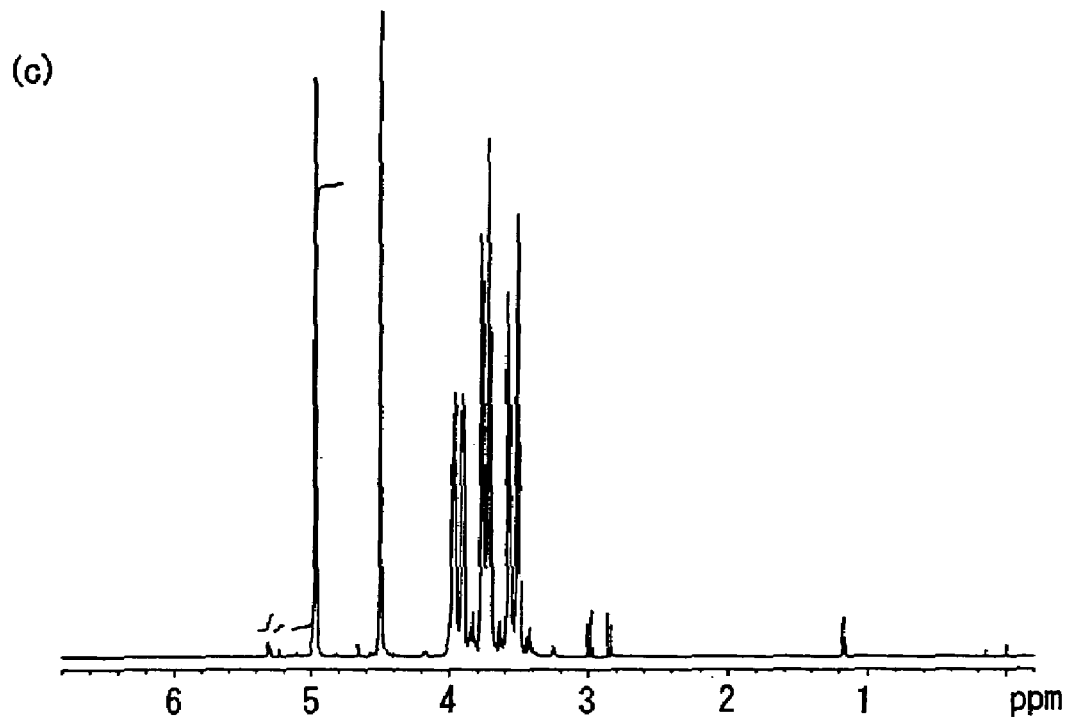
FIG. 3B shows diagrams showing the NMR spectra of glycogen contained in a composition of the present invention.
Figure 3B:
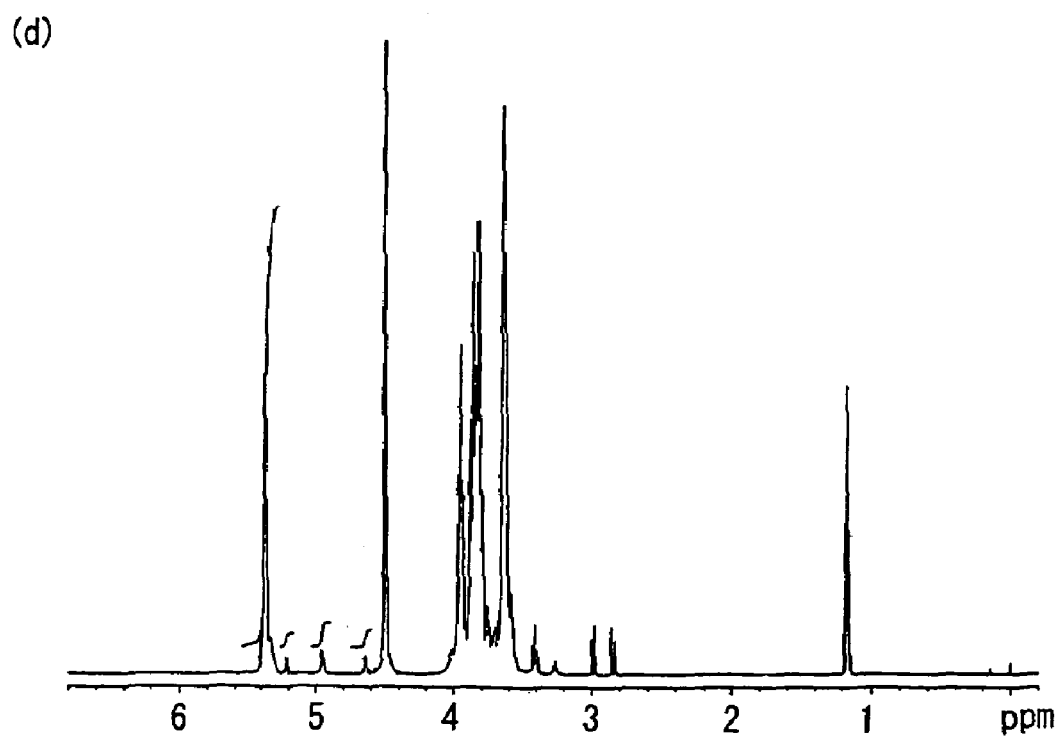

For purified glycogen from starch, anomeric proton peaks were observed at 5.37 ppm, 5.33 ppm and 4.95 ppm (FIG. 3B(d)). These peaks are in good agreement with the above-described anomeric proton peaks of the glycogen reagent.

The 5.37 ppm peak may be attributed to α1-4 linkage. The purified glycogen from starch generally showed high-resolution spectra having sharp peaks. This is because as described above, the purified glycogen from starch contains molecules having a molecular weight smaller than the glycogen reagent. α1-6 linkage accounts for about 8%.

(4) Purified Glycogen from Dextran

For purified glycogen from dextran, an anomeric proton peak was mainly observed at 4.97 ppm (FIG. 3B(c)). This peak is attributed to α1-6 linkage. Dextran is a glucose homopolysaccharide mainly containing α1-6 linkage. A peak at 5.3 ppm, which is attributed to α1-4 linkage, is small. For glycogen from dextran, such a peak is much smaller.

4. Monosaccharide Composition

Diastase was added to an aqueous solution of purified glycogen obtained from various sugar-containing materials in a manner similar to that of Example 13 to enzymatically degrade the purified glycogen. Each resultant degradation solution was spotted onto a silica gel plate, followed by TLC analysis using a mixture solution of isopropanol and purified water (16:4) as developing solvent. After development, the plate was recovered, followed by drying at room temperature. The plate was sprayed with dilute sulfuric acid solution, followed by heating at 115° C. for about 3 min.

As a result, any of the solutions, in which the purified glycogens were enzymatically degraded, showed an Rf value of 0.59 which is equal to that of glucose as a standard product (manufactured by Wako Pure Chemical Industries, Ltd.) (the results not shown). It was thus confirmed that any of the purified glycogens are a monosaccharide composition of glucose. On the other hand, purified glycogens from various sugar-containing materials were developed with the same solvent before enzymatic degradation. In this case, spots remained at the starting point (i.e., no development), as did the standard glycogen (Wako Pure Chemical Industries, Ltd.).

Example 12

Test for Improvement of Liver Function by Purified Glycogen

Mice were injected intraperitoneally with purified glycogen from Panax notoginseng obtained in a manner similar to that of section 2 of Example 10 so as to test for improvement of liver function in vivo.

1. Subjects

In vivo test were carried out using ICR induced male mice (manufactured by MDS Pharm Services, body weight 22±2 g).

2. Samples to be Tested

Purified glycogen and Silymarin (registered trademark) (manufactured by Sigma) were used as samples to be tested. Silymarin was a positive control which has a function of improving liver function. Glycogen and Silymarin were dissolved in 0.9% saline containing 2% Tween80 (registered trademark) (manufactured by Wako Pure Chemical Industries, Ltd.) to predetermined concentrations.

3. Doses 300 mg/kg or 400 mg/kg of purified glycogen was intraperitoneally injected per mouse (glycogen group). As controls, 10 mL/kg of 0.9% saline containing 2% Tween80 was intraperitoneally injected per mouse (control group). 100 mg/kg of the positive control Silymarin was intraperitoneally injected per mouse (Silymarin group).

4. Test Method

For each group, 5 ICR induced mice (22±2 g) were used. Each mouse was injected with carbon tetrachloride solution dissolved in 50% olive oil (0.1 mL/Kg) at once so as to induce liver disorder. 300 mg/kg or 400 mg/kg of each sample to be tested was intraperitoneally injected 30 min before, 4 hours after, and 8 hours after the injection of carbon tetrachloride. 24 hours after the final injection, the mice were sacrificed and the blood was collected. The serum GPT (SGPT) and GOT (SGOT) levels were measured with a commonly used a spectrophotometry method (a GPT measurement kit and a GOT measurement kit (manufactured by Wako Pure Chemical Industries, Ltd.) were used, respectively) using an autoanalyzer (ultraviolet assay).

5. Results of Experiments

The results of the measurement are shown in Table 6.

TABLE 6

Liver function improving function of purified glycogen from *Panax notoginseng*

| Test sample | Dose | SGPT (IU/L) | SGOT (IU/L) |
| --- | --- | --- | --- |
| Control | 10 mL/kh × 3 | 3506.4 ± 255.7(—) | 2681.6 ± 205.7(—) |
| Purified glycogen | 300 mg/kh × 3 | 3113.6 ± 123.1(11%) | 2287.2 ± 219.1(15%) |
|  | 400 mg/kg × 3 | 3158.4 ± 141.5(10%) | 2261.5 ± 127.5(16%) |
| Silymarin | 100 mg/kg × 3 | 1005.6 ± 140.2(71%) | 548.8 ± 76.5(80%) |

In Table 6, numerical figures (IU/L) are SGPT and SGOT averages of 5 mice for each group. Parenthesized values after averages indicate a reduction rate of the measurement result of each group relative to the measurement result of the control group.

The liver function improving function is generally identified when the levels of SGPT and SGOT values are lower than those of the control. As shown in Table 6, for the glycogen group, the 300 mg/Kg and 400 mg/Kg injections showed a reduction in SGPT by 10 to 11% and a reduction in SGOT by 15 to 16%, thereby indicating that the purified glycogen has a moderate liver function improving function. The positive control Silymarin showed a reduction in SGPT by 71% and a reduction in SGOT by 80%, i.e., a significant liver function improving function. Note that when SGPT and SGOT are reduced by 30% or more, a liver function improving function is judged to be significant.

Example 13

Test for Liver Function Improvement of Panax Notoginseng Extract

A liver function improvement test was carried out in the same method as described in Example 12, except that Panax notoginseng extract powder obtained as described in Example 1 was used. The results of the test are shown in Table 7.

TABLE 7

Liver function improving function of *Panax notoginseng* extract powder

| Test sample | Dose | SGPT(IU/L) | SGOT(IU/L) |
| --- | --- | --- | --- |
| Control | 10 mL/kg × 3 | 3752.4 ± 301.0(—) | 2097.6 ± 250.9(—) |
| Panax notoginseng extract powder | 300 mg/kg × 3 | 1096.8 ± 131.0(71%) | 656.4 ± 113.9(69%) |
| Silymarin | 100 mg/kg × 3 | 1603.2 ± 236.3(57%) | 764.4 ± 66.7(64%) |

Similar to Table 6, numerical figures (IU/L) in Table 7 are SGPT and SGOT averages of 5 mice for each group. Parenthesized values after averages indicate a reduction rate of the measurement result of each group relative to the measurement result of the control group.

As shown in Table 7, the Panax notoginseng extract group showed a reduction in SGPT by 71% and a reduction in SGOT by 69%. It was thus revealed that the Panax notoginseng extract shows a significant liver function improving function.

INDUSTRIAL APPLICABILITY

A method of producing glycogen is provided, which comprises heat- and pressure-treating polysaccharide, plants containing a large amount of starch, or the like under acidic conditions, where non-substrate specific and simple operations are only required. According to the method of the present invention, a variety of glycogens may be obtained from various materials. By analyzing the properties of these glycogens, raw materials available for food materials, infusion solution materials, and the like are provided.

Glycogen is known as an animal storage polysaccharide as well as a substance having an action of enhancing liver function. Further, there has been a report that glycogens extracted from cuttlefish, scallop, and the like have a potent anti-tumor activity. Thus, applications of the glycogen as new functional foods are expected.

Glycogen, particularly a low molecular weight glycogen of 10,000 or less, is provided. Glycogen obtained by a simple operation using plants containing a large amount of polysaccharide, such as starch or the like, starch, pullulan, dextran, or the like as a material, is provided.

What is claimed is:

1. A composition obtained from starch under a pressure of 1-1.3 kgf/cm$^2$ at 75 to 125° C. in the presence of organic acid comprising at least one glycogen as a major component, wherein said composition has a specific rotation of $[\alpha]_D$+197° and anomeric proton peaks at 5.37 ppm and 4.95 to 5.33 ppm in $^1$H NMR spectra.

2. A composition obtained from dextran under a pressure of 1-1.3 kgf/cm$^2$ at 75 to 125° C. in the presence of organic acid comprising at least one glycogen as a major component, wherein said composition has a specific rotation of $[\alpha]_D$+178° and anomeric proton peaks at 4.97 ppm and 5.22 to 5.33 ppm in $^1$H NMR spectra.

3. A composition obtained from Panax notoginseng under a pressure of 1-1.3 kgf/cm$^2$ at 75 to 125° C. in the presence of organic acid comprising at least one glycogen as a major component, wherein said composition has a specific rotation of $[\alpha]_D$+174° and anomeric proton peaks at 5.38 ppm and 4.96 ppm in $^1$H NMR spectra.

* * * * *